United States Patent [19]

Köpsel et al.

[11] 4,407,740

[45] Oct. 4, 1983

[54] DI- AND TETRA-HYDROBENZOFURANONES AS SCENTS AND AROMA SUBSTANCES

[75] Inventors: Manfred Köpsel; Roland Emberger, both of Holzminden, Fed. Rep. of Germany

[73] Assignee: Haarmann & Reimer GmbH, Holzminden, Fed. Rep. of Germany

[21] Appl. No.: 256,748

[22] Filed: Apr. 23, 1981

[30] Foreign Application Priority Data

May 3, 1980 [DE]  Fed. Rep. of Germany ....... 3017068

[51] Int. Cl.³ .......................... A61K 7/46; A23L 2/26
[52] U.S. Cl. ................... 252/522 R; 426/536; 131/277; 549/302
[58] Field of Search ............ 252/522 R; 260/343.3 R; 426/536; 131/277; 549/302

[56] References Cited

U.S. PATENT DOCUMENTS 3,850,963  11/1974  Thoma et al. ................. 252/522 R
3,970,673   7/1976  Kondo et al. ................. 260/343.3 R
4,113,891   9/1978  Winter et al. .

FOREIGN PATENT DOCUMENTS 46-42587  12/1971  Japan .................................. 426/536

OTHER PUBLICATIONS

Agricultural and Biological Chemistry, vol. 44, Jul. 1980, pp. 1535-1543.
Agr. Biol. Chem. vol. 37, 1973, pp. 2441-2442.
Journal of the American Medical Society, vol. 72, Jan. 1950, pp. 399-403, by R. B. Woodward et al.
Arctander, "Perfume and Flavor Materials of Natural Origin" Elizabeth, N.J., (1960), pp. 513-516.

Primary Examiner—John F. Niebling
Attorney, Agent, or Firm—Sprung, Horn, Kramer & Woods

[57]  ABSTRACT

Di- and tetrahydrobenzofuranone of the formula

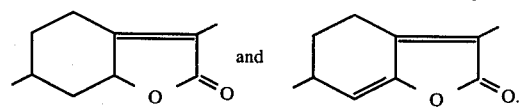

are useful in scenting and/or flavoring agents for imparting thereto a coumarin and coconut note.

7 Claims, No Drawings

DI- AND TETRA-HYDROBENZOFURANONES AS SCENTS AND AROMA SUBSTANCES

The present invention relates to the use of di- and tetra-hydrobenzofuranone derivatives as scents and flavor substances, and scenting and flavoring compositions containing these compounds.

The use of compounds of the general formula

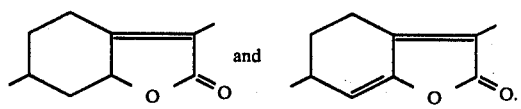

as scents and flavoring agents has been found.

These substances can be used for the preparation of perfume compositions and perfumed products and for the preparation of flavoring compositions.

The compounds of the general formula (I), that is to say 3,6-dimethyl-5,6-dihydro-2(4H)-benzofuranone and 3,6-dimethyl-5,6,7,7a-tetrahydro-2(4H)-benzofuranone are known from the literature, but their suitability as a scent and aroma substance has not been recognized. 3,6-Dimethyl-5,6-dihydro-2(4H)-benzofuranone, which is also called dehydromenthofurolactone in the literature, has been prepared by splitting off water from 7a-hydroxy-3,6-dimethyl-4,5,6,7-tetrahydro-2-benzofuranone, the autoxidation product of menthofuran (J. Am. Chem. Soc. 72, 399 (1950). 3,6-Dimethyl-5,6,7,7a-tetrahydro-2-(4H)-benzofuranone, also called menthofurolactone in the literature, has been prepared by hydrogenation of the autoxidation product with sodium borohydride (Tetrahedron 23, 2583 (1967). Furthermore, both compounds have been detected as being components of peppermint oil (Int. Congr. Essent. Oils, 6 th, 1974, 142).

The compounds to be used according to the invention are prepared in accordance with the following equation:

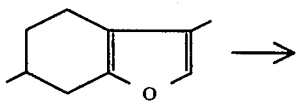
II

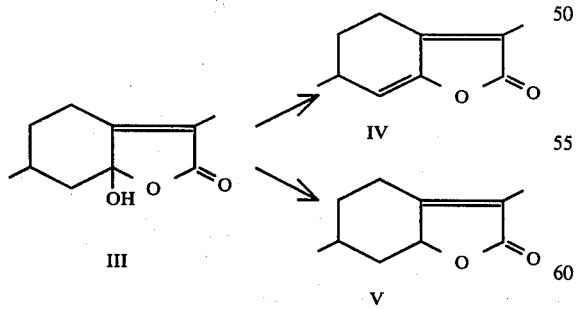

Menthofuran (II) is oxidized with atmospheric oxygen in a photooxidation reaction to give a hydroperoxide, which is decomposed in situ with sodium hydroxide solution to give 7a-hydroxy-3,6-dimethyl-4,5,6,7-tetrahydro-2-benzofuranone (III). 3,6-Dimethyl-5,6-dihydro-2(4H)-benzofuranone (IV) is obtained from the hydroxymenthofurolactone (III) by splitting off water, for example with sodium bisulphate (J. Am. Chem. Soc. 72, 399 (1950)). The reduction of the hydroxymenthofurolactone (III) with, for example, sodium borohydride (Tetrahedron 23, 2583 (1967)) gives 3,6-dimethyl-5,6,7,7a-tetrahydro-2(4H)-benzofuranone (V).

The di- and tetra-hydrobenzofuranone derivatives to be used according to the invention are valuable scents which have, in addition to a sweet lactone-like note, a distinct coumarin and coconut note. They can very easily be combined with other substances to give novel scent compositions, in which they can be employed in amounts of about 1 to 50 percent by weight. relative to the total composition. The new compositions can be used for perfuming cosmetics, such as creams, lotions, aerosols and toilet soaps, and industrial products, such as washing agents and cleaning agents.

The compounds to be used according to the invention are also valuable flavoring substances which, because of their coumarin note, are particularly suitable for the preparation of aromas with a coumarin, woodruff and caramel flavor. These properties are particularly important because the use of coumarin itself for flavoring foodstuffs is severely restricted in many countries, and the compounds to be used according to the invention are greatly superior to dihydrocoumarin, which is at present the most common coumarin substitute. The flavoring compositions prepared using the di- and tetra-hydrobenzofuranone derivatives (III) and (IV) can be used in the entire range of foodstuffs in which the coumarin/woodruff flavor and caramel flavor is desired. They are particularly suitable for use in treacle, jelly, soft drinks, ice-cream, fondant compositions and the like. Moreover, they can advantageously be employed as a coumarin substitute for flavoring tobacco, since, in exactly the same manner as coumarin and coumarin-containing extracts, for example tonka bean extract and deertongue extract, they impart not only a hay/woodruff-like note to the smoke but also remove the unpleasant acridity from the smoke and have a rounding-off effect on the overall aroma.

The compounds to be used according to the invention are employed in amounts of 0.001 to 100 ppm, preferably 0.1 to 10 ppm, relative to the foodstuff ready for consumption or the finished tobacco mixture.

The following examples are intended to illustrate the subject of the invention in more detail, but without limiting it thereto:

EXAMPLE 1

A perfume composition with a fern note is prepared by mixing the following components:

| | |
|---|---|
| 200 | lavandin |
| 100 | bergamot identoil |
| 50 | linalyl acetate |
| 50 | lemon oil identoil |
| 100 | linalool |
| 20 | geranium oil identoil |
| 10 | rosemary oil |
| 10 | isoeugenol |
| 50 | cedarwood oil |
| 20 | patchouli oil |
| 50 | sandel H + R |
| 10 | oak moss absolue |
| 5 | labdanum absolue |
| 10 | cinnamyl alcohol |
| 10 | heliotropin |
| 10 | vanillin |
| 15 | musk ketone |

-continued

| | |
|---|---|
| 20 | musk ambrette |
| 20 | 1,3,4,6,7,8-hexahydro-4,6,6,7,8,8-hexamethyl-cyclopenta-γ-2-benzopyran |
| 760 | parts by weight |

The composition is rounded off by adding 50 parts by weight of 3,6-dimethyl-5,6,7,7a-tetrahydro-2(4H)-benzofuranone and thereby becomes more valuable in the perfumistic sense, and, as a result of the sweet base character of the scent, the perfume oil gains character and impact.

EXAMPLE 2

A base mixture A with a coumarin/woodruff flavor was prepared by mixing the following components:

| | |
|---|---|
| 12 | ethylvanillin |
| 60 | vanillin |
| 60 | anisaldehyde |
| 60 | methylcyclopentenolone |
| 70 | heliotropin |
| 738 | 1,2-propylene glycol |
| 1,000 | parts by weight |

Mixture B was obtained from mixture A by adding 190 parts by weight of dihydrocoumarin, while simultaneously reducing the amount of propylene glycol to 548 parts by weight.

Mixture C was obtained from mixture A by adding 18 parts by weight of 3,6-dimethyl-5,6-dihydro-2(4H)-benzofuranone, while simultaneously reducing the amount of propylene glycol to 720 parts by weight.

Mixture D was obtained from mixture A by adding 18 parts by weight of 3,6-dimethyl-5,6,7,7a-tetrahydro-2(4H) -benzofuranone, while simultaneously reducing the amount of propylene glycol to 720 parts by weight.

Mixtures A to D were sampled, in a dosage of 20 ppm in a 3.25% strength sugar solution in water, by a group of flavor testers. The description of the flavor of the individual mixtures was as follows:
A: slight coumarin/woodruff flavor
B: coumarin/woodruff flavor
C: more pronounced and more typical coumarin/woodruff flavor than A and B, at the same time milder and fuller.
D: more pronounced and more typical coumarin/woodruff flavor than A and B, at the same time milder and fuller.

EXAMPLE 3

A fine-cut tobacco mixture was flavored with mixtures A, C and D of Example 2 in a dosage of 0.05% In the sensory test, a distinct coumarin-like odor was detected on the tobacco when mixtures C and D were used. A distinct coumarin-like flavor note was likewise recognizable in the smoke. At the same time, the rounding-off and mellowing effect of these mixtures can also be detected.

Mixture A gave a considerably less typical coumarin note and had scarcely any rounding-off and mellowing effect.

EXAMPLE 4

A base mixture E with a caramel flavor was prepared by mixing the following components:

| | |
|---|---|
| 15 | diacetyl |
| 15 | ethylvanillin |
| 50 | heliotropin |
| 80 | vanillin |
| 80 | methylcyclopentenolone |
| 760 | 1,2-propylene glycol |
| 1,000 | parts by weight |

Mixture F was prepared by adding 2 parts by weight of 3,6-dimethyl-5,6-dihydro-2(4H)-benzofuranone, while simultaneously reducing the amount of propylene glycol to 758 parts by weight.

Mixture G was prepared by adding 2 parts by weight of 3,6-dimethyl-5,6,7,7a-tetrahydro-2(4H)-benzofuranone, while simultaneously reducing the amount of propylene glycol to 758 parts by weight.

Mixtures E to G were sampled at a dosage of 100 ppm in a 3.25% strength sugar solution in water by a group of flavor testers. The description of the flavor of the individual mixtures was as follows:
E: buttery and slightly caramelly
F: typical caramel character, considerably fuller and stronger than E
G: typical caramel character, considerably fuller and stronger than E It will be appreciated that the instant specification and examples are set forth by way of illustration and not limitation, and that various modifications and changes may be made without departing from the spirit and scope of the present invention.

We claim:

1. A scenting and/or flavoring composition comprising conventional scenting and/or flavoring agents or carriers and, as a scent and/or flavor modifier thereof, a modifying amount of a di- or tetra-hydrobenzofuranone of the formula

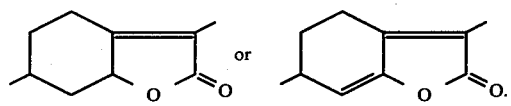

2. A composition according to claim 1, wherein the modifier is present in about 1 to 50% by weight.

3. A composition according to claim 1 which is a flavoring composition, the modifier being present in about 0.001 to 100 ppm.

4. A process for modifying the scent and/or flavor of a composition itself intended for scenting and/or flavoring, comprising adding thereto a di- or tetra-hydrobenzofuranone of the formula

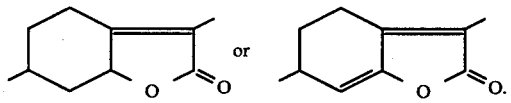

5. A process according to claim 4, wherein the scenting and/or flavoring composition is an intermediate to be combined with other scenting and/or flavoring intermediates and the hydrobenzofuranone is added in amount to constitute about 1 to 50% by weight of the scenting and/or flavoring composition.

6. A process according to claim 4, wherein the composition is a flavoring composition and the hydrobenzofuranone is added in about 0.001 to 100 ppm.

7. In the imparting of a coumarin or coconut scent and/or flavor to a composition by adding to such composition a scent—and/or flavor-modifying effective amount of a scenting and/or flavoring agent, the improvement which comprises employing as said agent a di- or tetra-hydrobenzoluranone of the formula

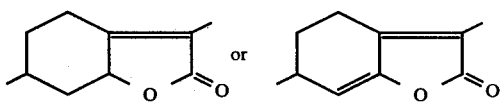

* * * * *